United States Patent
Ueno et al.

(10) Patent No.: US 9,605,110 B2
(45) Date of Patent: Mar. 28, 2017

(54) EPOXY RESIN CURING AGENT

(71) Applicant: MITSUBISHI GAS CHEMICAL COMPANY, INC., Tokyo (JP)

(72) Inventors: Shuichi Ueno, Tokyo (JP); Dai Oguro, Tokyo (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 1 day.

(21) Appl. No.: 14/439,757

(22) PCT Filed: Oct. 21, 2013

(86) PCT No.: PCT/JP2013/078464
§ 371 (c)(1),
(2) Date: Apr. 30, 2015

(87) PCT Pub. No.: WO2014/069273
PCT Pub. Date: May 8, 2014

(65) Prior Publication Data
US 2015/0291729 A1    Oct. 15, 2015

(30) Foreign Application Priority Data

Nov. 1, 2012  (JP) ................... 2012-241520
Nov. 1, 2012  (JP) ................... 2012-241521

(51) Int. Cl.
| | | |
|---|---|---|
| C08G 59/42 | (2006.01) | |
| C07D 307/60 | (2006.01) | |
| C08G 59/24 | (2006.01) | |
| C08K 5/134 | (2006.01) | |

(52) U.S. Cl.
CPC ....... *C08G 59/4238* (2013.01); *C07D 307/60* (2013.01); *C08G 59/24* (2013.01); *C08G 59/245* (2013.01); *C08G 59/4215* (2013.01); *C08K 5/1345* (2013.01)

(58) Field of Classification Search
CPC .................................. C08G 59/4238
See application file for complete search history.

(56) References Cited

U.S. PATENT DOCUMENTS

| | | | | |
|---|---|---|---|---|
| 3,795,658 A | * | 3/1974 | Thompson et al. | C08G 59/245 528/97 |
| 4,004,894 A | * | 1/1977 | Nohe ............... | C10L 1/1905 44/391 |
| 5,399,647 A | * | 3/1995 | Nozaki ............ | C07C 255/31 430/270.1 |
| 5,880,154 A | * | 3/1999 | Boukrinskaia ..... | C08F 8/12 514/561 |
| 6,042,991 A | * | 3/2000 | Aoai ............... | G03F 7/039 430/270.1 |
| 2003/0071366 A1 | | 4/2003 | Rubinsztajn et al. | |

FOREIGN PATENT DOCUMENTS

| | | |
|---|---|---|
| JP | 6-9756 | 1/1994 |
| JP | 6-32872 | 2/1994 |
| JP | 2006-206783 | 8/2006 |
| JP | 2008-120697 | 5/2008 |
| JP | 2011-219508 | 11/2011 |
| WO | 2006/077862 | 7/2006 |

OTHER PUBLICATIONS

Fukunishi et al., "Regioselective radical addition of adamantanes to dimethyl maleate", Department of Chemistry Kyoto Institute of Technology, Oct. 1988, pp. 826-827.
Search report from PCT/JP2013/078464, mail date is Jan. 21, 2014.

* cited by examiner

*Primary Examiner* — Megan McCulley
(74) *Attorney, Agent, or Firm* — Greenblum & Bernstein, P.L.C.

(57) ABSTRACT

The epoxy resin curing agent of the present invention comprises a compound represented by the following formula (1):

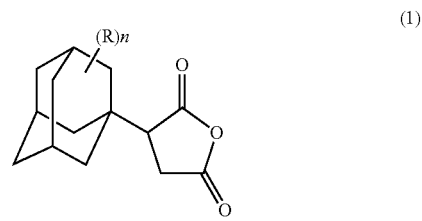

wherein R represents a methyl group, an ethyl group, or a hydroxyl group, and n is an integer of 1 to 3.

19 Claims, No Drawings

EPOXY RESIN CURING AGENT

TECHNICAL FIELD

The present invention relates to an epoxy resin curing agent, an epoxy resin composition, a cured product prepared by curing the composition, and a molded body comprising the cured product.

BACKGROUND ART

Liquid epoxy resins have a long history. Liquid epoxy resins used in combination with liquid curing agents have high handling properties. For this reason, such epoxy resins are useful and advantageous in that they can provide firm molded bodies in a simple manner, and are used as the resin alone or as a composite material. Because of these favorable properties, the epoxy resins are used in broad applications in a variety of fields, such as dental materials, a variety of structure materials, LED sealing materials, adhesives, and coating materials including hard coats (for example, see Patent Documents 1 and 2).

LIST OF PRIOR ART DOCUMENTS

Patent Document

Patent Document 1: Japanese Patent Laid-Open No. 6-32872
Patent Document 2: Japanese Patent Laid-Open No. 2006-206783

SUMMARY OF INVENTION

Problems to be Solved by Invention

Mainly in systems of acid anhydride-curing, when an epoxy resin called an alicyclic epoxy resin typified by CELLOXIDE CEL2021P manufactured by Daicel Corporation is used, the hardness and the heat resistance of the resulting molded bodies are enhanced. Examples of the most standard epoxy resins include bisphenol A (Bis A)-based diglycidyl ether such as jER828 manufactured by Mitsubishi Chemical Corporation. Bisphenol A (Bis A)-based diglycidyl ether has been widely used for a long time due to its favorable properties probably derived from the bisphenol A skeleton and the like.

In the systems of acid anhydride-curable epoxy resins, use of an alicyclic epoxy resin can attain molded bodies having high surface hardness. When the alicyclic epoxy resin is cured with MeHHPA (methyl hexahydrophthalic anhydride; such as HN-5500 manufactured by Hitachi Chemical Co., Ltd.), which is a standard low viscous liquid acid anhydride, the surface of the resulting cured product (molded body) has a pencil hardness of 2H, which is higher than that of the Bis A-based epoxy resin (hardness: H). When a molded body having high surface hardness is used as an outermost portion of a final product, the surface of the final product is barely scratched. Accordingly, the surface hardness of the molded body may often be a factor to determine the product life. The molecule structure of the alicyclic epoxy resin has no aromatic ring, and therefore the alicyclic epoxy resin has high coloring resistance to ultraviolet (UV) light. For this reason, when the alicyclic epoxy resin is used as a member for a product to be used on the premise that the product is irradiated with UV light, the product can attain a long life. Higher performance, however, has been required in various applications in recent years, leading to a demand for molded bodies formed of the alicyclic epoxy resin that surface hardness and coloring resistance to UV light should be further improved to widen the range of applications of the molded bodies.

In contrast, when Bis A-based diglycidyl ether is used, the resulting molded bodies have flexibility, impact resistance, and crack resistance higher than those of the molded bodies formed of the alicyclic epoxy resin, and further have high refractive index, which means higher performance in applications to optical transparent members used on the premise that they are not irradiated with UV light.

When Bis A-based diglycidyl ether is used, the glass transition temperature (Tg) of the resulting molded body is one of important physical properties. If the glass transition temperature (Tg) can be improved, the time to cool the molded body after pre-curing and before releasing of the molded body can be shortened and the number of molds can be reduced. In this case, if the same number of molds is used in a factory, the production speed increases and molding efficiency becomes higher. Namely, when Bis A-based diglycidyl ether is used, an improvement in the glass transition temperature (Tg) of the resulting molded body leads to an increase in efficiency to produce molded bodies. Such an improvement, however, is not sufficient yet, and further improvement has been required.

An object of the present invention is to further enhance the surface hardness and coloring resistance to UV light of the resulting cured product (molded body) using an alicyclic epoxy resin to attain the molded body that can be used in a broader range of applications. Another object of the present invention is to allow an improvement in Tg, which is one of physical properties of the resulting cured product (molded body), using Bis A-based diglycidyl ether.

Means for Solving Problems

As the result of extensive research to attain the objects above, the present inventors have found that if an acid anhydride having a specific structure is used as an epoxy resin curing agent, a variety of physical properties and performance of the resulting cured product can be enhanced, and have completed the present invention. Namely, the present invention is as follows.

1. An epoxy resin curing agent, comprising a compound represented by the following formula (1):

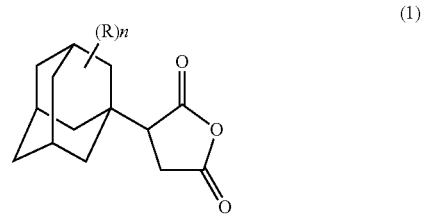

(1)

wherein R represents a methyl group, an ethyl group, or a hydroxyl group, and n is an integer of 1 to 3.

2. The epoxy resin curing agent according to Clause 1, wherein the compound represented by the above formula (1) is a compound represented by the following formula (2):

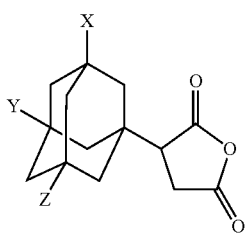

(2)

wherein X, Y, and Z each independently represent a hydrogen atom, a methyl group, an ethyl group, or a hydroxyl group.

3. The epoxy resin curing agent according to Clause 2, wherein the compound represented by the above formula (2) is a compound represented by the following formula (3):

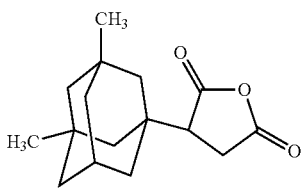

(3)

4. The epoxy resin curing agent according to Clause 2, wherein the compound represented by the above formula (2) is a compound represented by the following formula (4):

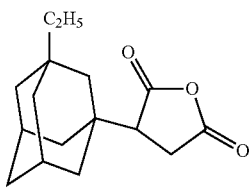

(4)

5. An epoxy resin composition comprising an epoxy resin and the curing agent according to any one of Clauses 1 to 4.

6. The epoxy resin composition according to Clause 5, wherein the epoxy resin is at least one selected from the group consisting of alicyclic epoxy resin, nuclear-hydrogenated Bis A-based diglycidyl ether, and Bis A-based diglycidyl ether.

7. The epoxy resin composition according to Clause 5 or 6, wherein an equivalent ratio of the curing agent to the epoxy resin (equivalent of the curing agent/equivalent of the epoxy resin) is 0.5 to 1.2.

8. The epoxy resin composition according to any one of Clauses 5 to 7, further comprising a curing accelerator.

9. The epoxy resin composition according to any one of Clauses 5 to 8, further comprising an antioxidant.

10. The epoxy resin composition according to any one of Clauses 5 to 9, further comprising a UV absorber.

11. The epoxy resin composition according to any one of Clauses 5 to 10, further comprising an inorganic filler.

12. A cured product prepared by curing the epoxy resin composition according to any one of Clauses 5 to 11.

13. A molded body comprising the cured product according to Clause 12.

14. A compound represented by the following formula (4):

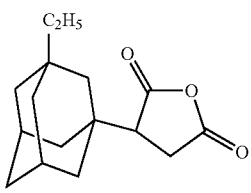

(4)

Advantages of Invention

According to the present invention, when the alicyclic epoxy resin is used, the resulting cured product (molded body) can have enhanced surface hardness and coloring resistance to UV light to attain higher performance, and therefore can be used in a broader range of applications.

According to the present invention, when Bis A-based diglycidyl ether is used, the resulting cured product (molded body) has improved Tg, which is one of physical properties. For this reason, the time to cool the molded body after pre-curing and before releasing of the molded body can be shortened and the number of molds can be reduced. In this case, if the same number of molds is used in a factory, the production speed increases and molding efficiency becomes higher. Accordingly, the present invention attains higher production efficiency of molded bodies, and widens the range of applications of the molded bodies.

MODE FOR CARRYING OUT INVENTION

Hereinafter, an embodiment of the present invention (hereinafter, also referred to as "present embodiment") will be described in detail. The following embodiment is given in order to illustrate the present invention. The present invention is not limited to only the embodiment.

Hereinafter, the epoxy resin curing agent, the epoxy resin composition, the cured product prepared by curing the composition, the molded body etc. according to the present embodiment will be described.

[Epoxy Resin Curing Agent]

The epoxy resin curing agent of the present embodiment contains a compound represented by the following formula (1):

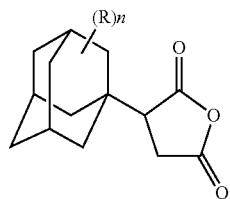

(1)

wherein R represents a methyl group, an ethyl group, or a hydroxyl group, and n is an integer of 1 to 3.

When an alicyclic epoxy resin is cured with the epoxy resin curing agent containing the compound represented by the above formula (1), the surface hardness and coloring resistance to UV light of the resulting cured product (molded body) are further enhanced. When Bis A-based diglycidyl ether is cured with the epoxy resin curing agent containing the compound represented by the above formula (1), the glass transition temperature (Tg) of the resulting cured product (molded body) is improved.

The epoxy resin curing agent of the present embodiment preferably contains a compound represented by the following formula (2):

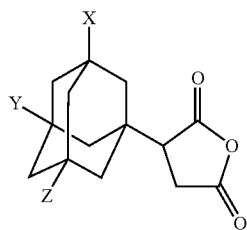

(2)

wherein X, Y, and Z each independently represent a hydrogen atom, a methyl group, an ethyl group, or a hydroxyl group.

When an alicyclic epoxy resin is cured with the epoxy resin curing agent comprising the compound represented by the above formula (2), the surface hardness and coloring resistance to UV light of the resulting cured product (molded body) are more significantly enhanced. When Bis A-based diglycidyl ether is cured with the epoxy resin curing agent comprising the compound represented by the above formula (2), the glass transition temperature (Tg) of the resulting cured product (molded body) is more significantly improved.

More preferably, the epoxy resin curing agent of the present embodiment is at least one selected from the group consisting of maleic anhydride monoadduct to dimethyladamantane represented by the following formula (3):

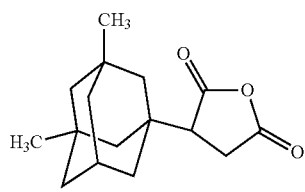

(3)

and maleic anhydride monoadduct to monoethyladamantane represented by the following formula (4):

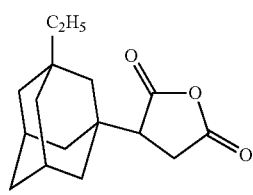

(4)

When an alicyclic epoxy resin is cured with an epoxy resin curing agent comprising the compound represented by the above formula (3) and/or the compound represented by the above formula (4), the surface hardness and coloring resistance to UV light of the resulting cured product (molded body) are more significantly enhanced. When Bis A-based diglycidyl ether is cured with an epoxy resin curing agent comprising the compound represented by the above formula (3) and/or the compound represented by the above formula (4), the glass transition temperature (Tg) of the resulting cured product (molded body) is more significantly improved.

The epoxy resin curing agents of the present embodiment can be used singly or in combinations of two or more.

The epoxy resin curing agent of the present embodiment may contain an additional acid anhydride-based epoxy resin curing agent, amine-based epoxy resin curing agent, and phenol-based epoxy resin curing agent as a component for the curing agent as long as the advantages of the present invention are not impaired. These may be used singly or in combinations of two or more.

Examples of the acid anhydride-based epoxy resin curing agent include, but not particularly limited to, tetrahydrophthalic anhydride, hexahydrophthalic anhydride, methyltetrahydrophthalic anhydride, methylhexahydrophthalic anhydride, methyl nadic anhydride, trialkyltetrahydrophthalic anhydride, methylcyclohexenetetracarboxylic dianhydride, phthalic anhydride, trimellitic anhydride, pyromellitic anhydride, benzophenonetetracarboxylic dianhydride, ethylene glycol bisanhydrotrimellitate, glycerol (anhydrotrimellitate) monoacetate, dodecenylsuccinic anhydride, aliphatic dibasic polyanhydride, chlorendic anhydride, and hydrogenated compounds of the above acid anhydride. These may be contained singly or in combination.

Examples of the amine-based epoxy resin curing agent include, but not particularly limited to, aliphatic amines such as diethylenetriamine, triethylenetetramine, N-aminoethylpiperazine, menthenediamine, isophoronediamine, and m-xylylenediamine; and aromatic amines such as m-phenylenediamine, 4,4'-diaminodiphenylmethane, and 4,4'-diaminodiphenyl sulfone.

Examples of the phenol-based epoxy resin curing agent include, but not particularly limited to, phenol novolac resins, cresol novolac resins, bisphenol novolac resins, and triazine-modified phenol novolac resins.

[Method of Producing Compound Represented by Formula (1)]

The compound represented by the above formula (1) can be prepared by radical addition of maleic anhydride to an adamantane compound.

Examples of the adamantane compound as a raw material used in the present embodiment include, but not particularly limited to, adamantane, methyladamantane, dimethyladamantane, trimethyladamantane, ethyladamantane, diethyladamantane, triethyladamantane, adamantanol, adamantanediol, and adamantanetriol. Among these, dimethyladamantane or ethyladamantane is preferred from the viewpoint of the pot life before curing and the coloring properties of the cured product.

As for the molar ratio of the raw materials to be used, the adamantane compound is used in the range of preferably 1 to 20 mol, more preferably 1.5 to 15 mol, still more preferably 1.5 to 10 mol per mol of maleic anhydride.

During radical addition of maleic anhydride to the adamantane compound, the reaction temperature is in the range of preferably 120 to 180° C., more preferably 130 to 170° C., still more preferably 150 to 170° C.

The reaction time after dropwise addition of a radical generator is in the range of preferably 0.1 to 10 hours, more preferably 0.5 to 5 hours, still more preferably 1 to 3 hours.

The amount of the radical generator used in the present embodiment is in the range of preferably 0.001 to 0.1 mol, more preferably 0.005 to 0.05 mol, still more preferably 0.02 to 0.07 mol per mol of maleic anhydride. Examples of preferred radical generators include di-tert-butyl peroxide, benzoyl peroxide, and azobisisobutyronitrile. Among these, di-tert-butyl peroxide is more preferred.

The adamantane compound and maleic anhydride used in the present embodiment can be reacted in the absence of a solvent or in a solvent. Examples of the solvent to be used include, but not particularly limited to, dichlorobenzene, cyclohexanone, and dibutyl ether. Preferably, the reaction is performed in the absence of the solvent for operational reasons.

The reaction product thus prepared can be refined by distillation, crystallization, or column separation.

Specific preferred conditions will be described below. First, dimethyladamantane or ethyladamantane and maleic anhydride are placed in a reaction container at the molar ratio of the former to the later of 1.6:1, and the inner temperature of the reaction container is kept at about 160° C. Next, a radical generator such as di-tert-butyl peroxide (5.5 mmol) is dissolved in a small amount of dimethyladamantane or ethyladamantane to prepare a solution, and the solution is added dropwise into the reaction container over about 3 hours. The reaction is completed in about 3 hours after completion of the dropwise addition. A reaction product is prepared. The resulting reaction product is distilled under reduced pressure to prepare a corresponding target product. The ratio of the raw materials to be used, the reaction temperature and the reaction time specifically mentioned above can be properly varied so as to attain the target product at a higher yield, and another radical generator may be used.

[Epoxy Resin Composition]

The epoxy resin composition of the present embodiment contains an epoxy resin (hereinafter sometimes referred to as a "base resin") and the epoxy resin curing agent above. For example, the base resin used in the present embodiment is, but not particularly limited to, at least one selected from the group consisting of alicyclic epoxy resin, nuclear-hydrogenated Bis A-based diglycidyl ether, and Bis A-based diglycidyl ether. If such an epoxy resin is used as the base resin, the effect of the epoxy resin curing agent described above is more significantly demonstrated to more significantly enhance the properties of the resulting cured product.

In the present embodiment, the alicyclic epoxy resin indicates an epoxy resin having an alicyclic ring in the molecule in which the carbon-carbon bonds forming the alicyclic ring are partially shared with an epoxy ring. Examples of the alicyclic epoxy resin include, but not particularly limited to, 3,4-epoxycyclohexylmethyl-3',4'-epoxycyclohexane carboxylate, and vinylcyclohexene diepoxide. Specific examples thereof include CELLOXIDE CEL2021P manufactured by Daicel Corporation.

Examples of nuclear-hydrogenated Bis A-based diglycidyl ether include, but not particularly limited to, YX8000 manufactured by Mitsubishi Chemical Corporation. Examples of Bis A-based diglycidyl ether include, but not particularly limited to, jER828 manufactured by Mitsubishi Chemical Corporation.

Examples of other epoxy resins include, but not particularly limited to, glycidyl ethers having one epoxy group such as bisphenol F-based epoxy resins, cresol novolac-based epoxy resins, phenol novolac-based epoxy resins, biphenyl-based epoxy resins, stilbene-based epoxy resins, hydroquinone-based epoxy resins, naphthalene skeleton-based epoxy resins, tetraphenylolethane-based epoxy resins, DPP-based epoxy resins, trishydroxyphenylmethane-based epoxy resins, dicyclopentadienephenol-based epoxy resins, diglycidyl ether of bisphenol A-ethylene oxide adducts, diglycidyl ether of bisphenol A-propylene oxide adducts, phenyl glycidyl ether, and cresyl glycidyl ether. Examples of the epoxy resins include nuclear-hydrogenated epoxy resins which are nuclear-hydrogenated products of these epoxy resins. These epoxy resin components may be used singly or in combinations of two or more by mixing. An oxetane resin copolymerizable with the epoxy resin or a variety of modified resins can be used.

In the epoxy resin composition of the present embodiment, the total content of the epoxy resin and the epoxy resin curing agent is preferably 20 to 100% by mass, more preferably 50 to 100% by mass, still more preferably 80 to 100% by mass.

In the epoxy resin composition of the present embodiment, the mixing proportion of the epoxy resin and the epoxy resin curing agent is preferably adjusted such that the equivalent ratio of the curing agent to the epoxy resin (equivalent of the curing agent/equivalent of the epoxy resin) falls within the following range. The equivalent ratio of the curing agent to the epoxy resin (equivalent of the curing agent/equivalent of the epoxy resin) is in the range of preferably 0.5 to 1.2, more preferably 0.7 to 1.1, still more preferably 0.8 to 1.0. When the equivalent ratio (equivalent of the curing agent/equivalent of the epoxy resin) is within the above range, the resulting cured product tends to have high Tg, high heat resistance, and high UV resistance. Through the present specification, the term "equivalent" indicates an equivalent on the basis of acid anhydride group (1 mol)/glycidyl ring (1 mol)=equivalent ratio of 1, on the premise that an acid anhydride group —$CH_2$—CO—O—CO—$CH_2$— is reacted with a glycidyl ring (epoxy ring) at a ratio of 1:1.

In the epoxy resin composition of the present embodiment, the equivalent ratio of the curing agent to the epoxy resin (equivalent of the curing agent/equivalent of the epoxy resin) can be determined by measuring the equivalent of the epoxy resin (epoxy equivalent) and the equivalent of the curing agent (acid anhydride equivalent) separately, and calculating the values obtained from the measurement. The epoxy equivalent can be determined according to JIS K7236 by potentiometry with a standard solution of 0.1 mol/L perchloric acid in acetic acid. The acid anhydride equivalent can be determined by component analysis with a nuclear magnetic resonance apparatus (NMR) and a gas chromatography (GC) and calculation of the results of analysis.

The epoxy resin composition of the present embodiment may optionally contain, as necessary, a variety of additives such as curing accelerators, antioxidants, UV absorbers, inorganic fillers, resin reforming agents, and silane coupling agents in the range so as not to impair advantages of the present invention. These additives may be used singly or in combinations of two or more.

Examples of the curing accelerator include, but not particularly limited to, tertiary amines such as benzyldimethylamine, tris(dimethylaminomethyl)phenol, and dimethylcyclohexylamine; imidazoles such as 1-cyanoethyl-2-ethyl-4-methylimidazole, 2-ethyl-4-methylimidazole, and 1-benzyl-2-methylimidazole; organic phosphorus-based compounds such as triphenylphosphine and triphenyl phosphite; quaternary phosphonium salts such as tetraphenylphosphonium bromide and tetra-n-butylphosphonium bromide; diazabicycloalkenes such as 1,8-diazabicyclo[5.4.0]undecene-7 and organic acid salts thereof; organic metal compounds such as zinc octylate, tin octylate, and aluminum acetacetone complexes; quaternary ammonium salts such as tetraethylammonium bromide and tetrabutylammonium bromide; boron compounds such as boron trifluoride and triphenyl borate; and metal halides such as zinc chloride and stannic chloride. Latent curing accelerators typified by the followings also can be used: high melting point dispersing latent accelerators such as amine addition-based accelerators prepared by adding high melting point imidazole compounds, dicyandiamide, and amine to epoxy resins; microcapsule-based latent accelerators prepared by coating the surfaces of imidazole-based, phosphorus-based, and phosphine-based accelerators with polymers; amine salt-based latent curing accelerators; and high temperature dissociation-based thermal cationic polymerizable latent curing accelerators such as Lewis acid salts and Bronsted acid salts. These curing accelerators may be used singly or in combinations of two or more by mixing.

In the epoxy resin composition of the present embodiment, the content of the curing accelerator is preferably 0.01 to 10% by mass, more preferably 0.05 to 5% by mass, still more preferably 0.1 to 3% by mass.

The antioxidant can enhance the thermal stability of the resulting cured product more significantly. Examples of the antioxidant include, but not particularly limited to, phenol-based antioxidants (such as dibutylhydroxytoluene), sulfur-based antioxidants (such as mercaptopropionic acid derivatives), phosphorus-based antioxidants (such as 9,10-dihydro-9-oxa-10-phosphaphenanthrene-10-oxide). Among these, phenol-based antioxidants can be suitably used. These additives may be used singly or in combinations of two or more by mixing.

In the epoxy resin composition of the present embodiment, the content of the antioxidant is preferably 0.01 to 10% by mass, more preferably 0.05 to 5% by mass, still more preferably 0.1 to 3% by mass.

Examples of the UV absorber include, but not particularly limited to, benzotriazole-based UV absorbers typified by TINUVIN P and TINUVIN 234 manufactured by BASF SE; triazine-based UV absorbers such as TINUVIN 1577ED; and hindered amine-based UV absorbers such as CHIMASSOLV 2020FDL.

In the epoxy resin composition of the present embodiment, the content of the UV absorber is preferably 0.01 to 10% by mass, more preferably 0.05 to 5% by mass, and still more preferably 0.1 to 3% by mass.

Examples of the inorganic filler include, but not particularly limited to, glass fiber, carbon fiber, titanium oxide, alumina, talc, mica, and aluminum hydroxide.

In the epoxy resin composition of the present embodiment, the content of the inorganic filler is preferably 0.01 to 80% by mass, more preferably 0.01 to 50% by mass, still more preferably 0.1 to 20% by mass.

Examples of the resin reforming agent include, but not particularly limited to, diluents such as n-butyl glycidyl ether, phenyl glycidyl ether, glycidyl methacrylate, vinylcyclohexene dioxide, diglycidyl aniline, and glycerol triglycidyl ether; and flexibility giving agents such as polypropylene glycidyl ether, polymerized fatty acid polyglycidyl ether, polypropylene glycol, and urethane prepolymers.

In the epoxy resin composition of the present embodiment, the content of the resin reforming agent is preferably 0.01 to 80% by mass, more preferably 0.01 to 50% by mass, still more preferably 0.1 to 20% by mass.

Examples of the silane coupling agent include, but not particularly limited to, chloropropyltrimethoxysilane, vinyltrichlorosilane, γ-methacryloxypropyltrimethoxysilane, and γ-aminopropyltriethoxysilane.

In the epoxy resin composition of the present embodiment, the content of the silane coupling agent is preferably 0.01 to 20% by mass, more preferably 0.05 to 10% by mass, still more preferably 0.1 to 5% by mass.

The method for curing the epoxy resin composition described above is not particularly limited, and any known curing apparatus such as a sealed curing furnace and a tunnel furnace enabling continuous curing can be employed, for example. Any known heating method such as circulation of hot air, heating with infrared radiation, and high-frequency heating can be used in the curing.

The curing temperature is preferably in the range of 80 to 250° C. and the curing time is preferably in the range of 30 seconds to 10 hours. To reduce the internal stress of the cured product, it is preferred that pre-curing is performed at 80 to 120° C. for 0.5 hours to 5 hours, and then post-curing is performed at 120 to 180° C. for 0.1 hours to 5 hours. To perform the curing in a short time, the epoxy resin composition is preferably cured in a condition of 150 to 250° C. for 30 seconds to 30 minutes.

For the epoxy resin composition of the present embodiment, two or more packs, i.e., a pack containing acid anhydride and a pack containing an epoxy resin may be separately preserved, and may be blended before the curing. Alternatively, the epoxy resin composition of the present embodiment may be preserved as a thermosetting composition containing the respective components, and may be used as it is in the curing. The epoxy resin composition of the present embodiment as the thermosetting composition is preferably preserved at a low temperature (usually −40 to 15° C.)

[Cured Product, Molded Body]

The cured product of the present embodiment is prepared by curing the above-described epoxy resin composition. The curing method has been described as above. In the cured product of the present embodiment, higher performance of the epoxy resin can be attained, and the surface hardness, the coloring resistance to UV light, and the glass transition temperature can be improved by use of the above-described epoxy resin curing agent. For example, the cured product of the present embodiment preferably has a pencil hardness of 3H or more. For the coloring resistance to UV light, the time taken to decrease the light transmittance at 400 nm to 70% is preferably 450 hours or more. The glass transition temperature is preferably 130° C. or more.

In particular, when an alicyclic epoxy resin is used as the base resin in the cured product of the present embodiment, the surface hardness and the coloring resistance to UV light are remarkably enhanced. When a Bis A-based epoxy resin is used as the base resin in the cured product of the present embodiment, the glass transition temperature is remarkably improved.

The molded body of the present embodiment contains the above-described cured product. The molded body of the present embodiment is suitably used in a variety of applications because of its excellent properties such as surface hardness and coloring resistance to UV light.

The epoxy resin composition, the cured product, or the molded body of the present embodiment is suitably used in applications of transparent members or the like (such as adhesives, coating materials, LED sealing materials, and transparent plates) because of these favorable properties.

[Compound]

The compound of the present embodiment is a compound represented by the following formula (4):

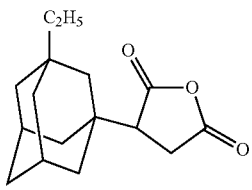

(4)

The compound represented by the above formula (4) is extremely useful as the epoxy resin curing agent, for example. When an alicyclic epoxy resin is cured with the epoxy resin curing agent containing the compound represented by the above formula (4), the surface hardness and coloring resistance to UV light of the resulting cured product (molded body) are more significantly enhanced. When Bis A-based diglycidyl ether is cured with the epoxy resin curing agent containing the compound represented by the above formula (4), the glass transition temperature (Tg) of the resulting cured product (molded body) is more significantly improved.

EXAMPLES

Next, the present invention will be specifically described by way of Examples. The present invention, however, will not be limited by these Examples.

The method of curing the epoxy resin composition and methods of measuring physical properties will be described below.

<Curing Method>

The epoxy resin compositions prepared in Examples and Comparative Examples described later were each stirred with a stirrer in a beaker. An inert gas present in the epoxy resin composition was degased under vacuum. Subsequently, the epoxy resin composition was injected into a silicone mold of a 50 mm square having a depth of 3 mm. The epoxy resin composition was pre-cured in a hot air dryer at 120° C. for 3 hours, and was then post-cured at 150° C. for 2 hours to prepare a cured product.

<Measurement of Glass Transition Temperature (Tg)>

The glass transition temperature (Tg) was measured with a thermal analysis system EXSTRA6000 TMA (thermal mechanical analyzer) manufactured by Seiko Instruments Inc. Specifically, under an $N_2$ stream, a sample was compressed and expanded at a temperature raising rate of 10° C./min from 30° C. to 260° C. (first time), and was compressed and expanded at a temperature raising rate of 10° C./min from 30° C. to 330° C. (second time), and the glass transition temperature (Tg) was measured. From the result of the second measurement, Tg was determined.

<Measurement of Pencil Hardness>

According to JIS K 5400, the pencil hardness was measured by scratching with pencils.

<Test on Coloring Resistance to UV Light>

A test on coloring resistance to UV light was performed as follows: a cured product was placed in a test furnace of I-Super UV tester SUV-W11 manufactured by DAINIPPON PLASTICS CO., LTD. Under a 55° C./50 RH % condition, the cured product was irradiated with light in a wavelength range of 295 to 450 nm (having the highest intensity peak at 360 to 380 nm) at a light intensity of an irradiated surface of 68 $mW/cm^2$.

<Measurement of Light Transmittance>

Before and after the test on coloring resistance to UV light, the light transmittance of the cured product was measured with a spectrophotometer [spectrophotometer UV-3100 manufactured by SHIMADZU Corporation]. Before and after the test on coloring resistance to UV light, the refractive index of the cured product was measured with a Multi-Wavelength Abbe Refractometer DR-M2 manufactured by ATAGO CO., LTD. From the measured light transmittance and the surface reflectance calculated from the refractive index separately measured, the light transmittance at 400 nm of the cured product (corresponding to a thickness of 1 mm) was determined. The measurement was repeated to determine the irradiation time in the test on coloring resistance to UV light until the light transmittance at 400 nm of the cured product after the test on coloring resistance to UV light became 70% or less of the light transmittance at 400 nm of the cured product before the test on coloring resistance to UV light.

Synthetic Example 1

Preparation of Maleic Anhydride Monoadduct to Dimethyladamantane [DMAMA] (Epoxy Resin Curing Agent)

Dimethyladamantane (1.6 mol) and maleic anhydride (1 mol) were placed in a reaction container, and the inner temperature of the reaction container was kept at 160° C. Di-tert-butyl peroxide (5.5 mmol) was dissolved in a small amount of dimethyladamantane to prepare a solution as a radical generator, and the solution was added dropwise into the reaction container over 3 hours to perform a reaction. The reaction was completed in 3 hours after the dropwise addition was completed. A reaction product was prepared. The resulting reaction product was distilled under reduced pressure to prepare a corresponding target product (maleic anhydride monoadduct to dimethyladamantane). After the reaction was completed, the resulting yield of maleic anhydride monoadduct to dimethyladamantane determined by gas chromatography (GC yield) was 45 mol % (in terms of maleic anhydride). The resulting maleic anhydride monoadduct to dimethyladamantane was used as an epoxy resin curing agent in Examples and Comparative Examples described later.

The resulting maleic anhydride monoadduct to dimethyladamantane was identified with a nuclear magnetic resonance spectrum ($^1$H-NMR, manufactured by JEOL, Ltd., 100 MHz). The result of identification is shown below.

$^1$H-NMR ($CCl_4$/TMS) δ 0.85 (s, 6H, $CH_3$); 1.1-1.7 (m, 13H); 2.0-2.7 (m, 3H, $CH_2$, CH)

Synthetic Example 2

Preparation of Maleic Anhydride Monoadduct to Monoethyladamantane [ETAMA] (Epoxy Resin Curing Agent)

Ethyladamantane (1.6 mol) and maleic anhydride (1 mol) were placed in a reaction container, and the inner temperature of the reaction container was kept at 160° C. Di-tert-butyl peroxide (5.5 mmol) was dissolved in a small amount of ethyladamantane to prepare a solution as a radical generator, and the solution was added dropwise into the reaction container over 3 hours to perform a reaction. The reaction was completed in 3 hours after the dropwise addition was completed. A reaction product was prepared. The resulting reaction product was distilled under reduced pressure to prepare a corresponding target product (maleic anhydride monoadduct to monoethyladamantane). After the reaction was completed, the GC yield of the resulting maleic anhydride monoadduct to ethyladamantane was 63 mol % (in terms of maleic anhydride). The maleic anhydride monoadduct to ethyladamantane was used as an epoxy resin curing agent in Examples and Comparative Examples described later.

The resulting maleic anhydride monoadduct to monoethyladamantane was identified with a nuclear magnetic resonance spectrum ($^1$H-NMR, manufactured by JEOL, Ltd., 100 MHz). The result of identification is shown below.

$^1$H-NMR (CCl$_4$/TMS) δ 0.90 (t, 3H, CH$_3$); 1.1-1.7 (m, 16H); 2.0-2.7 (m, 3H, CH$_2$, CH)

Example 1

DMAMA/Bis A-Based Epoxy Resin

The maleic anhydride monoadduct to dimethyladamantane (DMAMA) prepared in Synthetic Example 1 (35.1 parts by mass) described above, Bis A-based epoxy resin (manufactured by Mitsubishi Chemical Corporation, jER828) (27.7 parts by mass), quaternary phosphonium bromide (manufactured by San-Apro Ltd., U-CAT5003) (0.146 parts by mass), and a phenol-based antioxidant AO-50 (manufactured by ADEKA CORPORATION) (0.509 parts by mass) were mixed to prepare a resin composition (equivalent of the curing agent/equivalent of the epoxy resin=0.90). The resulting resin composition was cured by the above-described curing method to prepare a cured product.

The resulting cured product had a Tg of 138° C.

Comparative Example 1

MH700G/Bis A-Based Epoxy Resin

A mixture of hexahydrophthalic anhydride and methyl hexahydrophthalic anhydride (manufactured by New Japan Chemical Co., Ltd., MH700G) (30.0 parts by mass), Bis A-based epoxy resin (manufactured by Mitsubishi Chemical Corporation, jER828) (37.2 parts by mass), quaternary phosphonium bromide (manufactured by San-Apro Ltd., U-CAT5003) (0.197 parts by mass), and a phenol-based antioxidant AO-50 (manufactured by ADEKA CORPORATION) (0.544 parts by mass) were mixed to prepare a resin composition (equivalent of the curing agent/equivalent of the epoxy resin=0.90). The resulting resin composition was cured by the above-described curing method to prepare a cured product.

The resulting cured product had a Tg of 122° C.

Example 2

DMAMA/Alicyclic Epoxy Resin

The maleic anhydride monoadduct to dimethyladamantane (DMAMA) prepared in Synthetic Example 1 (42.0 parts by mass) described above, an alicyclic epoxy resin (3,4-epoxycyclohexylmethyl-3',4'-epoxycyclohexane carboxylate: manufactured by Daicel Corporation, CEL2021P) (22.5 parts by mass), quaternary phosphonium bromide (manufactured by San-Apro Ltd., U-CAT5003) (0.175 parts by mass), and a phenol-based antioxidant AO-50 (manufactured by ADEKA CORPORATION) (0.526 parts by weight) were mixed to prepare a resin composition (equivalent of the curing agent/equivalent of the epoxy resin=0.90). The resulting resin composition was cured by the above-described curing method to prepare a cured product.

The resulting cured product was subjected to the test on coloring resistance to UV light. The irradiation time until the light transmittance at 400 nm of the cured product became 70% or less was 450 hours.

The resulting cured product had a pencil hardness of 3H.

Example 3

ETAMA/Alicyclic Epoxy Resin

The maleic anhydride monoadduct to monoethyladamantane (ETAMA) prepared in Synthetic Example 2 described above (25.4 parts by mass), an alicyclic epoxy resin (3,4-epoxycyclohexylmethyl-3',4'-epoxycyclohexane carboxylate: manufactured by Daicel Corporation, CEL2021P) (13.6 parts by mass), quaternary phosphonium bromide (manufactured by San-Apro Ltd., U-CAT5003) (0.110 parts by mass), and a phenol-based antioxidant AO-50 (manufactured by ADEKA CORPORATION) (0.313 parts by mass) were mixed to prepare a resin composition (equivalent of the curing agent/equivalent of the epoxy resin=0.90). The resulting resin composition was cured by the above-described curing method to prepare a cured product.

The resulting cured product was subjected to the test on coloring resistance to UV light. The irradiation time until the light transmittance at 400 nm of the cured product became 70% was 460 hours.

The resulting cured product had a pencil hardness of 3H.

Comparative Example 2

MH700G/Alicyclic Epoxy Resin

A mixture of hexahydrophthalic anhydride and methyl hexahydrophthalic anhydride (manufactured by New Japan Chemical Co., Ltd., MH700G) (36.0 parts by mass), an alicyclic epoxy resin (3,4-epoxycyclohexylmethyl-3',4'-epoxycyclohexane carboxylate: manufactured by Daicel Corporation, CEL2021P) (30.0 parts by mass), quaternary phosphonium bromide (manufactured by San-Apro Ltd., U-CAT5003) (0.229 part by weight), and a phenol-based antioxidant AO-50 (manufactured by ADEKA CORPORATION) (0.534 parts by mass) were mixed to prepare a resin composition (equivalent of the curing agent/equivalent of the epoxy resin=0.90). The resulting resin composition was cured by the above-described curing operation method to prepare a cured product.

The resulting cured product was subjected to the test on coloring resistance to UV light. The irradiation time until the light transmittance at 400 nm of the cured product became 70% was 220 hours. The irradiation time was about a half of that in Example 2.

The resulting cured product had a pencil hardness of 2H.

INDUSTRIAL APPLICABILITY

Use of the epoxy resin composition comprising the epoxy resin curing agent of the present invention can attain a cured product exhibiting high surface hardness, high coloring resistance to UV light, and high Tg. The cured product can be suitably used in a variety of fields such as applications to LED sealing materials, adhesives, and coating materials.

The invention claimed is:

1. An epoxy resin curing agent comprising a compound represented by the following formula (4):

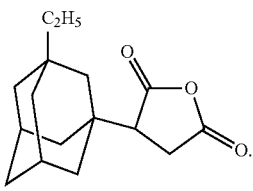

(4)

2. A compound represented by the following formula (4):

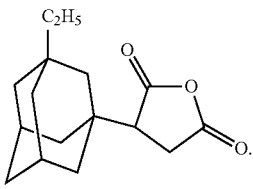

(4)

3. An epoxy resin composition comprising an epoxy resin, and an epoxy resin curing agent comprising a compound represented by the following formula (1):

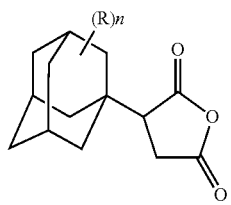

(1)

wherein R represents a methyl group, an ethyl group, or a hydroxyl group, and n is an integer of 1 to 3.

4. The epoxy resin composition according to claim 3, wherein the epoxy resin is at least one selected from the group consisting of alicyclic epoxy resin, nuclear-hydrogenated Bis A diglycidyl ether, and Bis A diglycidyl ether.

5. The epoxy resin composition according to claim 4, wherein an equivalent ratio of the curing agent to the epoxy resin (equivalent of the curing agent/equivalent of the epoxy resin) is 0.5 to 1.2.

6. The epoxy resin composition according to claim 4, further comprising a curing accelerator.

7. The epoxy resin composition according to claim 4, further comprising an antioxidant.

8. The epoxy resin composition according to claim 4, further comprising a UV absorber.

9. The epoxy resin composition according to claim 4, further comprising an inorganic filler.

10. The epoxy resin composition according to claim 3, wherein an equivalent ratio of the curing agent to the epoxy resin, equivalent of the curing agent/equivalent of the epoxy resin, is 0.5 to 1.2.

11. The epoxy resin composition according to claim 3, further comprising a curing accelerator.

12. The epoxy resin composition according to claim 3, further comprising an antioxidant.

13. The epoxy resin composition according to claim 3, further comprising a UV absorber.

14. The epoxy resin composition according to claim 3, further comprising an inorganic filler.

15. A cured product prepared by curing the epoxy resin composition according to claim 3.

16. A molded body comprising the cured product according to claim 15.

17. An epoxy resin composition of claim 3, wherein the compound represented by the above formula (1) is a compound represented by the following formula (2):

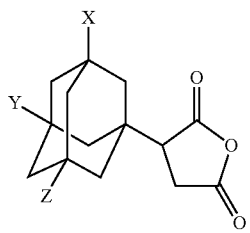

(2)

wherein X, Y, and Z each independently represent a hydrogen atom, a methyl group, an ethyl group, or a hydroxyl group.

18. The epoxy resin composition according to claim 17, wherein the compound represented by the above formula (2) is a compound represented by the following formula (3):

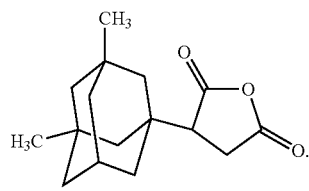

(3)

19. The epoxy resin composition according to claim 17, wherein the compound represented by the above formula (2) is a compound represented by the following formula (4):

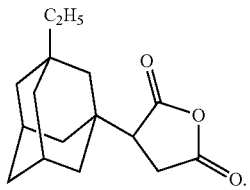

(4)

* * * * *